(12) United States Patent
Ludescher et al.

(10) Patent No.: US 7,253,320 B2
(45) Date of Patent: Aug. 7, 2007

(54) PROCESS FOR PREPARING POLYMORPHIC FORM II OF SERTRALINE HYDROCHLORIDE

(75) Inventors: Johannes Ludescher, Breitenbach (AT); Josef Wieser, Polling (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 11/396,967

(22) Filed: Apr. 3, 2006

(65) Prior Publication Data

US 2006/0229472 A1 Oct. 12, 2006

(30) Foreign Application Priority Data

Apr. 7, 2005 (GB) .................. 0507090.9

(51) Int. Cl.
*C07C 211/00* (2006.01)

(52) U.S. Cl. ................................. 564/308

(58) Field of Classification Search ............... None
See application file for complete search history.

(56) References Cited

U.S. PATENT DOCUMENTS

| 4,536,518 | A | 8/1985 | Welch, Jr. et al. |
| 5,248,699 | A | 9/1993 | Sysko et al. |
| 6,452,054 | B2 | 9/2002 | Aronhime et al. |
| 6,495,721 | B1 | 12/2002 | Schwartz et al. |
| 6,500,987 | B1 | 12/2002 | Schwartz et al. |
| 6,552,227 | B2 | 4/2003 | Mendelovici et al. |
| 6,600,073 | B1 | 7/2003 | Schwartz et al. |
| 6,809,221 | B2 | 10/2004 | Mendelovici et al. |
| 6,858,652 | B2 | 2/2005 | Aronhime et al. |
| 6,897,340 | B2 | 5/2005 | Borochovitch et al. |
| 7,022,881 | B2 | 4/2006 | Schwartz et al. |
| 7,196,222 | B2 | 3/2007 | Schwartz et al. |
| 2006/0241189 | A1 | 10/2006 | Schwatz et al. |

FOREIGN PATENT DOCUMENTS

| GB | 367453 | | 1/1938 |
| IN | 192257 | * | 9/2000 |
| WO | WO 03/051818 | | 12/2001 |
| WO | WO 03/099761 | | 2/2003 |
| WO | WO 03/051818 | | 6/2003 |
| WO | WO 03/093217 | | 11/2003 |
| WO | WO 2005/012225 | | 7/2004 |
| WO | WO 05/012225 | | 2/2005 |

* cited by examiner

*Primary Examiner*—Johann Richter
*Assistant Examiner*—MLouisa Lao
(74) *Attorney, Agent, or Firm*—Stephen R. Auten

(57) ABSTRACT

The present invention relates to a new process for preparing sertraline hydrochloride form II.

9 Claims, No Drawings

PROCESS FOR PREPARING POLYMORPHIC FORM II OF SERTRALINE HYDROCHLORIDE

The present invention relates to a process for preparing polymorphic form II of (1S,4S)N-methyl-4-(3,4-dichlorophenyl)-1,2,3,4-tetrahydro-1-naphthalenamine hydrochloride (sertraline hydrochloride).

The solid state chemistry of sertraline hydrochloride is disclosed in several patents and patent applications and over twenty different polymorphic forms of sertraline hydrochloride are known. Sertraline hydrochloride form II is the form commercially used in pharmaceutical formulations.

The preparation of sertraline hydrochloride form II is first disclosed in U.S. Pat. No. 4,536,518 and U.S. Pat. No. 5,248,699. The method described in U.S. Pat. No. 5,248,699 for making form II is rapid crystallization of sertraline hydrochloride from an organic solvent such as isopropyl alcohol, hexane, acetone, ethylacetate, methylisobutylketone, glacial acetic acid and ethylacetate. An actual example is not disclosed in U.S. Pat. No. 5,248,699. According to the example in U.S. Pat. No. 4,536,518 an ethyl acetate/ether solution of the free sertraline base is treated with gaseous hydrogen. This method is difficult as disclosed in examples 13 to 16 of WO 03/051818 according to which form II could not be obtained repeating the procedure of U.S. Pat. No. 4,536,518.

If free sertraline base as starting material is used and hydrogen chloride in gaseous form or dissolved in an organic solvent or aqueous hydrochloric acid is added to the sertraline base in alcoholic solvents like isopropyl alcohol or n-butanol or in ketones like acetone or methyl isobutyl ketone, a very viscous gel is first obtained as described in WO 03/099761 and intensive stirring is necessary, sometimes for several hours, to achieve recrystallisation to form II. In example 8 of WO 03/099761 sertraline hydrochloride form II is obtained by recrystallisation of sertraline hydrochloride from a hot solution of N,N-dimethylformamide by adding acetone under intensive stirring. The intermediate gelatinous form makes the preparation of form II difficult and the product obtained can be contaminated with amorphic form or form I.

WO 03/093217 discloses a method for preparation of sertraline hydrochloride form II using a solution of sertraline base or a solution or slurry of sertraline mandelate in n-butanol as solvent and gaseous hydrogen chloride for salt formation, but the process itself is not easy to carry out. A constant flow of gaseous hydrogen chloride within a certain time is necessary and the temperature has to be kept substantially constant between 40° C. to about 45° C. during the gas flow and even during filtering the product. It is pointed out that when the gas flow lasts too long, traces of sertraline hydrochloride form I inconsistently appear in small amounts up to 3% weight of sertraline hydrochloride form I in the product. On the other hand a gas flow that is too fast may cause operational problems i.e. difficulty in stirring and also adversely affect the polymorphic purity. A mixture of sertraline hydrochloride form II and form I was obtained according to example 7 wherein the temperature during the gas flow was at 70° C. In example 8, the product was precipitated at 45° C. and the slurry, at first a gelly like solid was filtered after cooling to 10° C. yielding also a mixture of sertraline hydrochloride form II and form I.

WO2005/012225 discloses a process for the preparation of form II of sertraline hydrochloride using an amine hydrochloride to react with a solution of sertraline base or a salt thereof to form sertraline form II. Certain amine hydrochlorides may not be sufficient soluble in the reaction mixture or may not be sufficient acidic to induce complete sertraline hydrochloride formation.

Thus there is a need for preparing sertraline hydrochloride form II in highly pure form in an easy repeatable manner and under simple reaction conditions.

The present invention which provides a new process for preparing sertraline hydrochloride polymorphic form II obviates the disadvantages associated with the known processes. The reaction conditions of the process according to the invention are simple and sertraline hydrochloride form II is obtained in highly pure form and in very high yield. Particularly the formation of a gelly like solid intermediate is avoided because the non-gelatinous precipitate formed immediately crystallizes as form II.

Accordingly, the present invention relates to a process for preparing sertraline hydrochloride form II comprising the steps of:

a) providing a solution or suspension of sertraline base or a salt thereof in a suitable solvent;

b) adding a hydrochloride of an organic amide at a temperature in the range of from about 0° C. to about 120° C., and c) isolating the crystalline solid polymorphic form II of sertraline hydrochloride.

Any sertraline salt except sertraline hydrochloride is suitable for the process according to the invention. Sertraline mandelate is preferred.

Hydrochlorides of organic amides preferably used in the process according to the invention are $C_{1-4}$-aliphatic acid amides, $C_{1-4}$-aliphatic acid N—$C_{1-2}$-alkylamides, $C_{1-4}$-aliphatic acid N,N—$C_{1-2}$-dialkylamides, a 5 or 6 membered cyclic aliphatic amide and/or a 5 or 6 membered cyclic aliphatic N—$C_{1-2}$— amide, preferably dimethylacetamide hydrochloride and/or N-methylpyrrolidone hydrochloride. $C_{1-4}$-aliphatic acid means a linear or branched aliphatic acid having 1 to 4 C atoms. The hydrochloride of an organic amide may be added to the solution or suspension of sertraline base or a salt thereof as a solid or as a solution in a suitable organic solvent. The amount of the hydrogen chloride of an organic amide may be a stoichiometric amount or an excess, e.g. 1.1 to 2.0 equivalents compared to sertraline base or a salt therof.

Hydrochlorides of organic amides used in the process according to the invention have a sufficient solubility in the solvents used for the formation of sertraline form II. Further, there are no corrosion problems during the manufacturing process.

A preferred solvent or solvent mixture is selected from n-butanol, n-pentanol, n-hexanol, n-heptanol, n-octanol, $C_{5-6}$-aliphatic ketone, acetonitril, ethylenglycol $C_{1-2}$ dialkylethers and diethylenglycol $C_{1-2}$ dialkylethers.

The temperature during the salt formation can be in the range of from about 0° C. to about 120° C., preferably from about 15° to about 120° C. Optionally seeding with crystals of polymorphic form II can be performed before or after addition of a hydrogen chloride of an organic amide although seeds are usually not necessary even at a reaction temperature below room temperature. The yield after drying the product is in the range of about 94% to 98%.

The present invention provides a process for preparation of sertraline hydrochloride form II in highly pure form and sertraline hydrochloride form I is not detectable by conventional XRD.

EXAMPLES

Example 1

30 g sertraline base is dissolved in 450 ml acetonitrile at room temperature. To this solution a solution of 13.3 g dimethylacetamide hydrochloride in 150 ml acetonitrile is added under stirring within 15 minutes. While adding solution of dimethylacetamide hydrochloride sertraline hydrochloride precipitates nicely in the crystalline Form II. After stirring the suspension for another hour, the product is filtered off, washed twice with 50 ml acetone and dried at 50° C. under vacuum for three hours to yield 31.3 g (94%) of sertraline hydrochloride form II.

Example 2

20 g sertraline base is dissolved in 300 ml acetonitrile at room temperature. To this solution a solution of 9.75 g N-methylpyrrolidin-2-on hydrochloride in 100 ml acetonitrile is added under stirring within 15 minutes. After stirring for 45 minutes, the crystals are filtered off, washed twice with 40 ml acetone and dried at 50° C. under vacuum for three hours to yield 21.28 g (95%) of sertraline hydrochloride form II.

Example 3

3 g sertraline base is dissolved in 45 ml acetonitrile at room temperature. The solution is cooled to 0° C. whereby a suspension is formed. A solution of 1.33 g dimethylacetamide hydrochloride in 15 ml acetonitrile is added under stirring within one minute. During the addition of the solution the temperature increases to about 8° C. and sertraline hydrochloride precipitates. After stirring for one hour at 0° C. the crystalline product is filtered off and dried at 50° C. under vacuum to yield 3.28 g (98%) of sertraline hydrochloride form II.

Example 4

Example 3 is repeated but the solution of dimethylacetamide hydrochloride is added at 80° C. and after the addition of the salt the reaction mixture is stirred for 45 minutes. There is obtained 3.12 g (93%) of sertraline hydrochloride form II.

Example 5

A suspension of 3 g sertraline mandelate in 60 ml acetonitrile is stirred at room temperature and 0.9 g dimethylacetamide hydrochloride in solid form is added. The suspension changes during the addition of dimethylacetamide hydrochloride resulting in a suspension of crystalline sertraline hydrochloride form II. After stirring for about one hour, the product is filtered off and dried at 50° C. under vacuum to yield 2.0 g (90%) of sertraline hydrochloride form II.

Example 6

Example 5 is repeated but dimethylacetamide hydrochloride is replaced by 0.99 g of N-methyl-2-pyrrolidinone yielding 1.91 g (85%) of sertraline hydrochloride Form II.

Example 7

A suspension of 2 g sertraline mandelate in 40 ml methyl isobutyl ketone is heated at 80° C. and 0.6 g dimethylacetamide hydrochloride in solid form is added. The suspension is stirred at 80° C. for 30 minutes and then cooled down to room temperature. After stirring for about one hour, the product is filtered off and dried at 50° C. under vacuum to yield 1.41 g (94%) of sertraline hydrochloride Form II.

Example 8

3 g of sertraline base in 60 ml n-butanol are heated to 50° C. 1.21 g N,N-dimethylacetamide hydrochloride are added. The suspension is kept for approximately 10 min at 50° C. and is then allowed to cool to ambient temperature within 1 hour. The product is then isolated by filtration and dried at 50° C. under vacuum to yield 2.16 g (65%) of Sertraline hydrochloride form II.

Example 9

Example 8 is repeated but n-butanol is replaced by n-hexanol yielding 2.31 g (69%) of sertraline hydrochloride Form II.

Example 10

3 g sertraline base is dissolved in 60 ml n-heptanol at 50° C. 1.33 g dimethylacetamide hydrochloride is added. After 5 minutes sertraline hydrochloride starts to precipitate. The reaction mixture is stirred at 50° C. for 25 minutes and then cooled down to room temperature. The crystalline product is filtered off and dried at 50° C. under vacuum to yield 2.53 g (75%) of sertraline hydrochloride Form II.

Example 11

Example 10 is repeated but n-heptanol is replaced by n-octanol yielding 2.46 g (73%) of sertraline hydrochloride Form II.

The invention claimed is:

1. A process for preparing sertraline hydrochloride form II comprising the steps of:
   a) providing a solution or suspension of sertraline base or a salt thereof in a suitable solvent;
   b) adding a hydrochloride of an organic amide at a temperature in the range of from about 0° C. to about 120° C., and
   c) isolating the crystalline solid polymorphic form II of sertraline hydrochloride.

2. A process according to claim 1, wherein in step a) the solvent is selected from the group consisting of: a $C_{4-8}$-alcohol, a $C_{5-6}$-aliphatic ketone, acetonitrile, an ethyleneglycol $C_{1-2}$-dialkylether and a diethyleneglycol $C_{1-2}$-dialkylether.

3. A process according to claim 1, wherein the hydrochloride of the organic amide is added in solid form.

4. A process according to claim 1, wherein the hydrochloride of the organic amide is added as solution in a solvent selected from the group consisting of a $C_{4-8}$-alcohol, a $C_{5-6}$-aliphatic ketane, acetonitrile, an ethyleneglycol $C_{1-2}$-dialkylether and a diethyleneglycol $C_{1-2}$-dialkylether.

5. A process according to claim 1 wherein in step b) the hydrochloride of an organic amide is selected from the group consisting of a hydrochloride of a $C_{1-4}$-aliphatic acid amide, a $C_{1-4}$-aliphatic acid N—$C_{1-2}$-alkylamide, a $C_{1-4}$-aliphatic acid N,N—$C_{1-2}$-dialkylamide, a 5 membered cyclic aliphatic amide, a 6 membered cyclic aliphatic amide, a 5 membered cyclic aliphatic N—$C_{1-2}$-amide, and a 6 membered cyclic aliphatic N—$C_{1-2}$-amide.

6. A process according to claim 1 wherein a suspension of sertraline mandelate is used.

7. The process according to claim 1 wherein the organic amide is dimethylacetamide hydrochloride or N-methylpyrrolidone hydrochloride.

8. The process according to claim 2 wherein the solvent is n-butanol.

9. The process according to claim 1 wherein the solvent is n-butanol.

* * * * *